United States Patent [19]
Hite et al.

[11] Patent Number: 5,968,072
[45] Date of Patent: Oct. 19, 1999

[54] METHOD AND APPARATUS FOR COLD COMPRESSION TREATMENT OF WOUNDS

[75] Inventors: Larry Lee Hite, Plymouth; Stephen Michael Beck, Elkhart, both of Ind.

[73] Assignee: Medical Wraps, Inc., Elkhart, Ind.

[21] Appl. No.: 08/170,503

[22] Filed: Dec. 20, 1993

[51] Int. Cl.$^6$ ..................................................... A61F 7/02
[52] U.S. Cl. .......................... 606/202; 607/104; 607/114
[58] Field of Search ..................... 607/96, 104, 108–112, 607/114; 606/201–3; 128/686

[56] References Cited

U.S. PATENT DOCUMENTS

| | | | |
|---|---|---|---|
| 3,548,819 | 12/1970 | Davis et al. | 607/112 X |
| 3,683,902 | 8/1972 | Artemenko et al. | 607/104 X |
| 3,901,225 | 8/1975 | Sconce | 607/112 X |
| 4,747,409 | 5/1988 | Silen | 607/112 X |
| 5,228,448 | 7/1993 | Byrd | 128/686 X |

*Primary Examiner*—Cary O'Connor
*Attorney, Agent, or Firm*—Ryan M. Fountain

[57] ABSTRACT

An apparatus is provided for femoral artery compression having an inflatable bladder, a cooling member and a rigid panel disposed within a sterile envelope and securable to a patient about the wound site via a detachable strap. The envelope can be pre-cooled as a unit and located over the wound such that the rigid panel focuses compressive force against the artery, trapping it between the panel and the pelvic bone rim. The bladder is adjustably inflatable by a conventional squeeze bulb valve arrangement and forces the cooling member against the rigid panel and the tissue in the wound vicinity. The rigid panel includes ridge structure to restrict sliding movement with respect to the cooling member. The envelope includes separate chambers for each of these components so as to restrict their movement once the envelope has been properly positioned. The envelope and its components are preferably constructed from inexpensive materials such that the entire apparatus is conveniently disposable after a single use.

8 Claims, 2 Drawing Sheets

METHOD AND APPARATUS FOR COLD COMPRESSION TREATMENT OF WOUNDS

BACKGROUND AND SUMMARY OF THE INVENTION

The present invention relates generally to medical and therapeutic devices and, more particularly, to devices for regulating the temperature and applied pressure to body tissue. The present invention is particularly suited for use in closing cuts, punctures and incisions in the femoral artery incident to arterial access procedures.

The femoral artery is a preferred access site of arterial catheters and other devices inserted into the cardiovascular system for inspection and surgical procedures. Generally speaking, that artery is initially cut, punctured or otherwise opened to allow devices to be inserted into and along the artery for certain lengths. When the device is removed, the opening in the artery must be closed and sealed quickly and efficiently. There is considerable variance in the difficulty of this closure, depending, for example, upon the physical condition of the patient.

Properly done, the artery opening is closed and compressed just sufficiently to stop bleeding, but not compressed so far as to significantly constrict the flow of blood downstream of the artery opening. Often, this compression must be maintained for a considerable length of time in order for the healing process to progress sufficiently especially where the patient's blood has been subject to anti-clotting treatment incident to the surgery. Previously, this closure procedure has been done manually by a nurse applying pressure through his or her fingers while immersed in an ice field about the artery opening. In addition to lacking sterility and precision, on occasion this manual pressure must be maintained for several hours, effectively immobilizing the nurse along with the patient and being an extremely uncomfortable experience for the nurse.

Various apparatus have been suggested as alternative procedures, but each of these has had significant drawbacks. For example, bovine collagen patches will provide instant coagulation but require precise placement on the artery or else it will introduce blood clots into the blood stream. In addition to thus producing a major health risk, these patches tend to be relatively expensive.

Other apparatus are known which permit normal coagulation over extended lengths of time, but lack reliability and precise control over the amount of compression applied. For example, it has been suggested to apply various rigid clamps to the patient to provide consistent arterial pressure. However, such clamps require complete patient immobility over an extended period of time to avoid leakage and, thus, can be extremely uncomfortable for the patient. Further, such clamps fail to fully accommodate the normal pulsating motion of the artery itself. Various flexible corsets or belts have also been suggested, but these often require careful installation prior to surgery, are uncomfortable for the patient to wear for long periods of time, restrict patient transfer, preclude optimum application of ice or cold compresses, provide only an arbitrary pressure based upon component elasticity and/or substantially block visibility of the artery vicinity.

Accordingly, it is an object of this invention to provide a new and improved apparatus and method for femoral artery compression, including a device which:

1. is inexpensive to manufacture,
2. is minimally restrictive to visibility of the puncture area,
3. accommodates patient movement without significant loss of compression,
4. is comfortable for the patient to wear for extended periods of time,
5. provides precise pressure at a fixed location,
6. is readily adjustable with respect to applied pressure,
7. permits adequate application of pressure and reduced temperature without constant involvement of hospital staff,
8. is sterile and easy to install after the operation, and
9. is constructed of familiar components so as to be user friendly as well as easy to repair and adjust.

These and other objects of the present invention are attained by the provision of an apparatus for femoral artery compression having an inflatable bladder, a cooling member and a rigid panel disposed within a sterile envelope and securable to a patient about the wound site via a detachable strap. The envelope can be precooled as a unit and located over the wound such that the rigid panel focuses compressive force against the artery, trapping it between the panel and the pelvic bone rim. The bladder is adjustably inflatable by a conventional squeeze bulb valve arrangement and forces the cooling member against the rigid panel and the tissue in the wound vicinity. The rigid panel includes ridge structure to restrict sliding movement with respect to the cooling member. The envelope includes separate chambers for each of these components so as to restrict their movement once the envelope has been properly positioned. The envelope and its components are preferably constructed from inexpensive materials such that the entire apparatus is conveniently disposable after a single use.

Other objects, advantages and novel features of the present invention will now be readily apparent to those of skill in the art from the attached drawings and detailed description below.

DETAILED DESCRIPTION OF PREFERRED EMBODIMENTS

Figure 1:
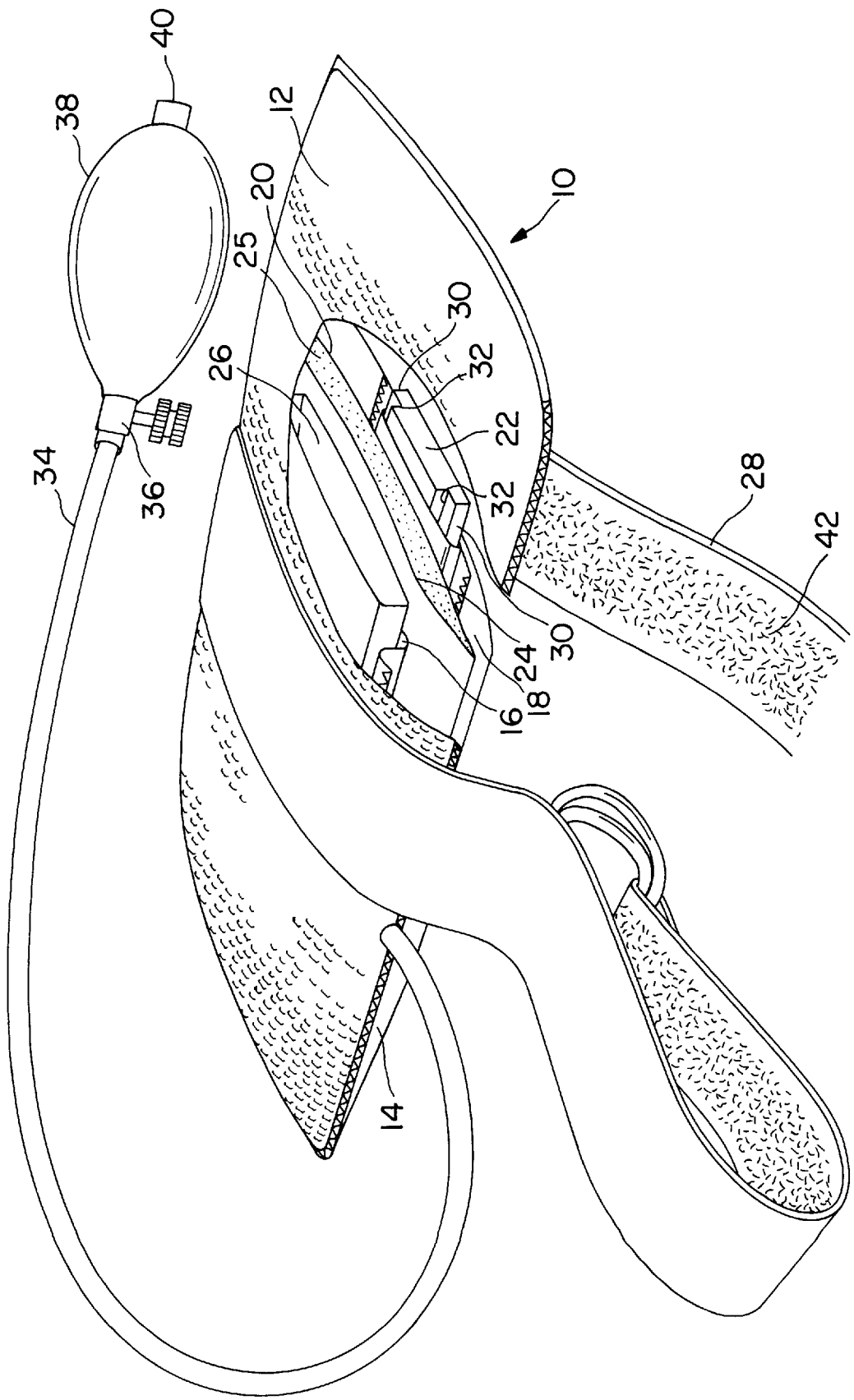
FIG. 1 shows a front, left perspective view of an assembled apparatus according to the present invention with a portion of the envelope broken away to reveal internal assembly.

FIG. 1, which illustrates a preferred embodiment of the present invention, shows a packaging element or envelope 10 having a top surface 12 and a bottom surface 14. Envelope 10 is formed to define internal chambers 16, 18 and 20. As shown, chamber 16 is adjacent top surface 12, chamber 20 is adjacent bottom surface 14 and chamber 18 defines the enclosure between those former two chambers.

As assembled, envelope 10 includes rigid panel 22, self contained coolant element or cooling member 24 and inflatable bladder 26. Panel 22 is preferably mounted within chamber 20, with bladder 26 mounted within chamber 16 and cooling member 24 mounted within chamber 18. Strap or belt member 28 is provided for use in combination with envelope 10.

Envelope 10 is preferably formed from a sterile fabric, such as 100% polyester sold by Singer Retail of Salsbury Manufacturing, subsidiary of Fab Industries, located in Madison, N.Y., with chambers 16 and 20 created by sewn panels. Bottom surface 14, for example, is intended to come into contact with body tissue and exposes that sterile fabric, while top surface 12, being used to securely engage and retain strap 28, is covered with an adhering material, such as Velcro hooks.

Rigid panel 22 is preferably formed from a plastic materials, such as ultra high molecular weight polyethylene of the type sold under the brand name CADCO by Cadillac Plastic co. of Troy, Mich. Strictly speaking, however, panel 22 does not need to be formed from only rigid materials; any other such firm material which focusses the pressure will suffice. As to the preferred embodiment shown, circumferential ledge 30 is disposed, for example, along the side of panel 22 furthest from cooling member 24, Thus, a step 32 is formed about panel 22 which faces cooling member 24. When panel 22 and cooling member 24 are compressed toward each other, step 32 serves to limit relative movement between those two elements.

Cooling member 24 is preferably a self contained package having a refrigerable liquid 25 therein. One such suitable device is the Therma-Kool Compress, a commercially available product of Nortech Laboratories, Inc. of Hicksville, N.Y.

Inflatable bladder 26 is preferably formed from conventional elastomeric or rubber material and includes a connecting conduit 34 connected via a rapid release valve 36 to a squeeze bulb 38. In operation and composition these elements resemble the components used in a conventional blood pressure measuring wrap. For example, air enters opening 40 of squeeze bulb 38 and is prevented from leaving through that opening because of an internal one way valve at opening 40. Squeezing of bulb 38 forces the air therein to exit bulb 38 and travel along conduit 34 to fill bladder 26. Another internal one way valve precludes that air from returning to bulb 38 when the bulb is released. To deflate bladder 26, valve 36 is opened and the air returns along conduit 34 to exit to atmosphere from that valve, upstream from bulb 38.

Figure 2:
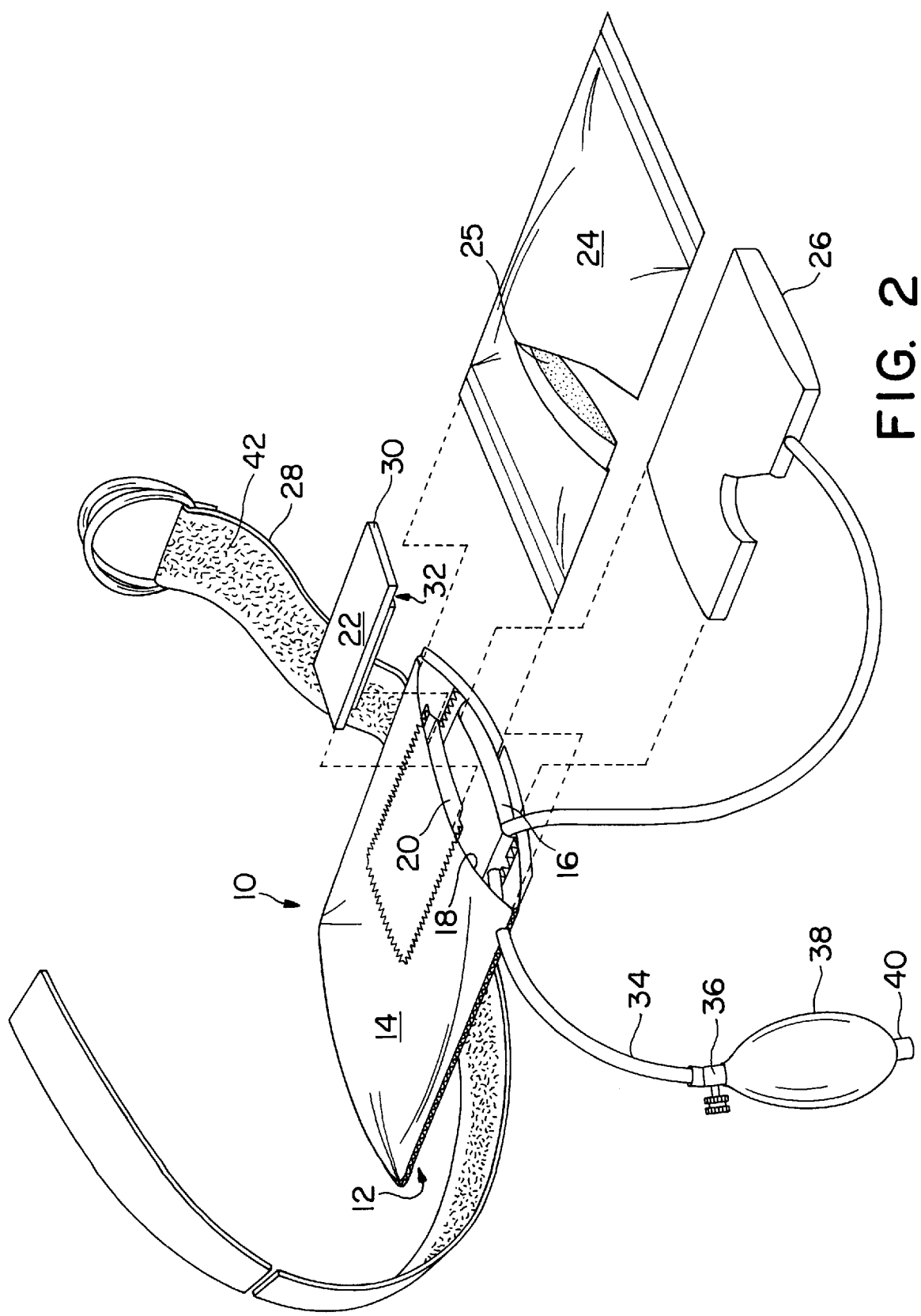
FIG. 2 shows a bottom, right perspective view of an apparatus according to the present invention with the front end of the envelope removed and the internal elements withdrawn.

As shown by a comparison of the different connections of conduit 34 shown in FIGS. 1 and 2, conduit 34 can be joined to bladder 26 at any desired location, although preferably this occurs to coincide with one or another side seam of envelope 10. Further, an auxiliary device, which as a pressure gauge, can be mounted along conduit 34, if desired for visibly precise monitoring of applied pressure.

Strap 28 preferably includes a fibrous material 42, such as is commonly used to connect with Velcro hook elements, on one side thereof. In addition to forming a secure connection with top surface 12, fibrous material 42 increases the comfortability of strap 28 to the wearer. In the examples shown, the width of strap 28 is significantly less than the width of top surface 12 such that strap 28 is selectively positionable at a variety of locations and orientations with respect to top surface 12.

Preparatory to use, envelope 10, including all elements therein, but not necessary strap 28, are refrigerated or frozen. Immediately after arterial surgery, initial arterial closure can be accomplished by the fingers of an attendant doctor or nurse. Thereafter, the present invention is positioned over the incision and pressed into place manually over the fingers used for initial compression. As those fingers are removed, preferably panel 22 is urged against the artery to trap it adjacent the pelvic bone such that compression is firm and easily controllable.

Thus positioned manually with respect to the artery, strap 28 is applied to envelope 10 and about the patient's body to secure that position. Alternatively, strap 28 can be positioned beneath the patient prior to application of envelope 10 and then secured to the envelope once the envelope is positioned. Thereafter, the desired amount of pressure is applied via squeeze bulb 38 such that manual pressure is no longer needed. As an alternative method of use, the nurse's fingers can remain on this incision until squeeze bulb 38 is used to inflate bladder 26. Where obese patients are involved it can be advantageous to also use a "belt loop" patch secured to the patient by adhesive in order to assist in positive location of the belt with respect to the patient.

Valve 36 permits relief adjustment of that pressure if needed, and squeeze bulb 38 readily permits increased pressure on demand (as, for example, when the reduced temperature causes contraction of the tissue). When visual inspection of the wound is desired, the reduced dimension of strap 28 and resilient flexibility of envelope 10 provide no significant hinderance to lifting away a portion of envelop 10, as if a flap. If desired, the present invention can also be used in conjunction with an arterial clamp especially as to anchor that clamp and chill adjacent tissue.

By way of additional advantage, the present invention's application of cold pressure to tissue adjacent the wound reduces the temperature of that wound quickly. Thus, it has been found that healing time is reduced and patient discomfort is minimized. Since the entire unit is precooled and disposable, maintenance, preparation time and training for usage are also minimized. Further, using components already familiar to hospital personnel makes this device user friendly, easier to repair and less likely to be misapplied.

Despite its structural simplicity, however, the present invention provides a reliable means of incrementally applying precise amounts of cold pressure to a fixed location for a long period of time and is relatively insensitive to limited patient movement. Thus, precise control over the incision closure and arterial blood flow during healing is available without full time attention by a doctor or nurse. Since it is applied mechanically, the closure pressure does not vary with fatigue of the attending nurse. Further, in the event complications arise, the present invention can be easily removed from the wound site.

Although preferred embodiments of the present invention have been described above in detail, that description is by way of illustration and example only, and not by way of limitation. Those of ordinary skill in the art will readily understand from this disclosure that various other uses and embodiment are anticipated by the present invention. For example, use is not exclusive to arterial incisions. Any medical procedure requiring adjustable pressure at a fixed location and/or cold compression can benefit from the present invention. In addition, modifications are envisioned with respect to the specific structure shown in the drawings, such as using rectangular cinch rings in preferred embodiments instead of the "D" rings shown.

Further, with regard to injuries requiring cold compression, as, for example, may types of muscle injuries incident to athletic events, teachings of the present invention can also be applied. As an illustration, an inflatable wrap, such as is typically used for blood pressure measurement about a limb, can be placed within a disposable sleeve of sterile material having a pocket for also receiving a cooling element. That cooling element is positioned over the affected tissue and the wrap is then disposed over the cooling element and around the adjacent body part, in place, for example, secured by mating Velcro strips on the sleeve. Air pressure is again provided by a squeeze bulb, and as swelling of the tissue decreases because of the cooling element, additional pressure is provided to maintain the wrap in place.

Accordingly, the spirit and scope of the present invention are limited only by the terms of the claims below.

What is claimed is:

1. An apparatus comprising:

flexible envelope member having therein at least first, second and third partitioned chambers, an inflatable bladder element disposed at least in part in said first chamber, a self contained coolant element disposed at least in part in said second chamber, and a rigid panel element disposed at least in part in said third chamber.

2. The apparatus according to claim 1 wherein said first, second and third chambers are disposed with respect to each other such that inflation of said bladder element applies pressure to said coolant element and said panel element which urges said coolant element and said panel element away from said bladder element.

3. The apparatus according to claim 1 wherein said envelope member includes a first and a second exterior side, said first exterior side being formed from a sterile material; said apparatus further comprises strap means for securing said envelope member in a predeterminable location, said second exterior side being formed from a material which adheres to said strap means.

4. The apparatus according to claim 1 wherein said panel element includes means for limiting movement thereof relative to said envelope member when said bladder element is inflated.

5. An apparatus for simultaneously applying increased pressure and reduced temperature to body tissue, comprising:

a flexible envelope, an inflatable bladder, a cooling member, and a rigid panel, each disposed within said envelope, and means for adjustably inflating and deflating said bladder, said bladder being disposed with respect to said cooling member and said rigid panel such that inflation of said bladder applies pressure to said cooling member and said rigid panel toward said body tissue.

6. The apparatus according to claim 5 further including means for retaining said envelope in substantially fixed relation to said body tissue.

7. The apparatus according to claim 6 wherein said means for retaining comprises an adhering surface disposed on said envelope and a strap element selectively positionable at a variety of locations on said adhering surface.

8. A femoral artery compression device for post operative use in closing an incision, puncture or cut in the femoral artery, comprising:

inflatable means for adjustably creating compressive pressure, first means for receiving said compressive pressure and applying that pressure to said femoral artery, self contained means for applying reduced temperatures at least to the tissue adjacent to said femoral artery, adjustable means for securing said first means and said self contained means to a predetermined location adjacent said femoral artery, wherein said inflatable means, first means, and self contained means are included at least in part within a packaging element for securing those means in fixed relative location, said packaging element including a sterile surface for engagement with body tissue adjacent said femoral artery, and wherein said inflatable means is disposed within said packaging element so as to also apply compressive pressure to said self contained means in a manner which urges said self contained means toward said femoral artery.

\* \* \* \* \*